US00PP23680P2

(12) United States Plant Patent
Deuter

(10) Patent No.: US PP23,680 P2
(45) Date of Patent: Jun. 18, 2013

(54) ***MISCANTHUS* PLANT NAMED 'MBS 1001'**

(50) Latin Name: ***Miscanthus* sp.**
Varietal Denomination: MBS 1001 (a.k.a. 'MDL 1001')

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 29 days.

(21) Appl. No.: 13/067,964

(22) Filed: Jul. 12, 2011

Related U.S. Application Data

(63) Continuation-in-part of application No. 12/584,496, filed on Sep. 4, 2009, now Pat. No. Plant 22,127, which is a continuation-in-part of application No. 12/387,444, filed on May 1, 2009, now Pat. No. Plant 22,033, and a continuation-in-part of application No. 12/387,429, filed on May 1, 2009, now Pat. No. Plant 22,047, and a continuation-in-part of application No. 12/387,437, filed on May 1, 2009, now abandoned.

(60) Provisional application No. 61/050,162, filed on May 2, 2008.

(51) Int. Cl.
*A01H 5/00* (2006.01)

(52) U.S. Cl.
USPC ..... Plt./384

(58) Field of Classification Search
USPC ..... Plt./384
See application file for complete search history.

(56) References Cited

U.S. PATENT DOCUMENTS

| | | | |
|---|---|---|---|
| PP13,008 | P2 | 9/2002 | Walsh |
| PP15,193 | P2 | 9/2004 | Smith et al. |
| PP16,197 | P2 | 1/2006 | Weiskott |
| PP18,161 | P2 | 10/2007 | Probst |
| PP22,033 | P2 | 7/2011 | Deuter |
| PP22,047 | P2 | 7/2011 | Deuter |
| PP22,127 | P2 | 9/2011 | Deuter |

OTHER PUBLICATIONS

U.S. Appl. No. 12/584,496, filed Sep. 4, 2009, Deuter.
U.S. Appl. No. 12/387,444, filed May 1, 2009, Deuter.
U.S. Appl. No. 12/387,429, filed May 1, 2009, Deuter.
U.S. Appl. No. 12/387,437, filed May 1, 2009, Deuter.
U.S. Appl. No. 12/387,437, Deuter.

*Primary Examiner* — Susan McCormick Ewoldt
(74) *Attorney, Agent, or Firm* — Cooley LLP

(57) ABSTRACT

A new and distinct cultivar of *Miscanthus* plant named 'MBS 1001', characterized by its vigorous growth rate, top leaf height, green-colored leaves, high biomass yield and high tiller density.

5 Drawing Sheets

Latin name of genus: *Miscanthus* sp.
Varietal denomination: 'MBS 1001' (a.k.a. 'MDL 1001').

BACKGROUND

The present disclosure relates to a new and distinct cultivar of hybrid *Miscanthus* originated as a cross from *Miscanthus sacchariflorus* (♀, 4n) and *M. sinensis* (♂, 2n) plants, and will be referred to hereafter by its cultivar name, 'MBS 1001.' 'MBS 1001' represents a new cultivar of *Miscanthus* species, a perennial grass which is grown for biomass production, building materials, livestock bedding, landscape use and ornamental value.

'MBS 1001', also known as 'MDL 1001', was selected for its vigorous growth from a selection field which was established from seedlings. The seedlings were obtained from seeds of a polycross of *Miscanthus sacchariflorus* (♀, 4n) and *M. sinensis* plants (♂, 2n). 'MBS 1001' was generated by crossing a single large-stemmed *M. sacchariflorus* genotype from Japan (accession No.: 93M0005064, ploidy: 4×) as a female parent with a population of 15 *M. sinensis* plants a pollen donors (accession Nos.: 93m0146002, 92M0179020, 92M1079017, 93M0147009, 92M0179016, 93m0146012, 93M0144001, 93m0146017, 92m0086, 92m0179015, 93m0146001, 93M0084, 93m0006005, 93M0006003, and 93m0007212; ploidy: 2×). From this cross, 158 seedlings were obtained and planted in a field. Based on field observations, a tetraploid variety having high biomass was selected and designated as 'MBS 1001'.

The commercial comparison to 'MBS 1001' is *M.×giganteus* cv. 'Illinois'. 'Illinois' was derived from a similar interspecific cross using different parental genotypes between *Miscanthus sacchariflorus* (4×) and *M. sinensis* (2×) resulting in a sterile clone plant selection that is available to the public.

'MBS 1001' is different from *Miscanthus* variety 'MBS 7001' ('Nagara') disclosed in U.S. Plant Pat. No. 22,033. 'MBS 1001' of the present application is 100% fertile, and is ~95% to 100% self-incompatible, and 95% to 100% cross-compatible. *Miscanthus* variety 'MBS 7001' ('Nagara') is a 98% to 100% sterile genotype, and is almost completely self- and cross-incompatible. Therefore, 'MBS 7001' rarely produces seed. In contrast, 'MBS 1001' produces significantly higher amounts of seed.

Fertile 'MBS 1001' is different from the commercial comparison *M.×giganteus* cv. 'Illinois'. 'Illinois' is considered to be a 100% sterile genotype, and is completely self- and cross-incompatible.

'MBS 1001' is also different from *Miscanthus* variety 'MBS 7002' ('Lake Erie') disclosed in U.S. Plant Pat. No. 22,047. 'MBS 1001' has greater seedling and vegetative plant vigor upon transplanting, and during spring greenup. It has slightly better cold tolerance than 'MBS 7002'. They are siblings and recombine very well in crossing. However, 'MBS 7002' is ~2 weeks later in flower initiation and over all seasonal maturity than 'MBS 1001'. 'MBS 1001' will go completely dormant during the short day winter months in the US, Canada and Europe.

'MBS 1001' is also different from *Miscanthus* variety 'MBS 7003' ('Columbia') disclosed in the co-pending U.S. Plant patent application Ser. No. 13/067,964, filed Jul. 12, 2011. 'MBS 1001' is 2-4 weeks later in flowering and maturity than 'MBS 7003'. 'MBS 1001' is ~0.75 m taller than 'MBS 7003' at seasonal maturity and maintains a taller growth habit during the entire growing season compared to 'MBS 7003'. They are siblings and recombine well to produce seed in bi-parental crossing.

'MBS 1001' is also different from *Miscanthus* variety 'MBS 1002' ('MDL 1002') disclosed in the U.S. Plant Pat. No. 22,127. 'MBS 1001' initiates flowering ~2 weeks earlier than 'MBS 1002'. They are siblings and recombine well to produce seed in bi-parental crossing.

'MBS 1001' was established asexually from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations.

SUMMARY

'MBS 1001' (a.k.a. 'MDL 1001')

The following traits have been repeatedly observed and represent the basic characteristics of the new cultivar. The new cultivar 'MBS 1001' has not been observed under all possible environmental conditions. The phenotype may vary somewhat with variations in temperature, day length, light intensity, soil types, and water and fertility levels without, however, any variance in genotype.

The following traits in combination distinguish this *Miscanthus* hybrid from *Miscanthus*×*giganteus* cv. 'Illinois' and ornamental *M. sinensis* forms. Plants for the botanical measurements in the present application are two to three-year-old plants. These plants would be considered as mature plants.

1. Vigorous growth
2. Top leaf height ~3.0-3.5 meters at 2 and 3 year maturity
3. Green leaves, no colored stripes are present
4. High biomass yield (~20-30 metric tons per hectare, equals to 9-13 U.S. tons per acre)
5. High tiller density 'MBS 1001' can be distinguished from the *Miscanthus* cultivars 'Strictus' (not patented, a.k.a 'Porcupine grass'), 'Super Stripe' (U.S. Plant Pat. No. 18,161), 'Gold Bar' (U.S. Plant Pat. No. 15,193), 'Little Zebra' (U.S. Plant Pat. No. 13,008), and 'Mysterious Maiden' (U.S. Plant Pat. No. 16,197) in that 'MBS 1001' has no stripes or colored bands on its leaves.

In side by side comparisons conducted at Klein-Wanzleben, Germany, 'MBS 1001' is more vigorous than either of its parent plants and produces more biomass than either parent. 'MBS 1001' has taller culms than both parents and demonstrates no lodging. The leaves stay longer on the culm compared to *M.*×*giganteus* cv. 'Illinois' and therefore, the leaf loss of 'MBS 1001' during winter is less which, in turn, leads to higher biomass yield.

'MBS 1001' can be propagated by rhizomes, from meristem or nodes. This further distinguishes 'MBS 1001' from *M. sinensis* in that *M. sinensis* cannot be propagated by nodes. 'MBS 1001' develops inflorescences and viable seed under optimal growing conditions.

BRIEF DESCRIPTION OF THE DRAWINGS

The accompanying color photographs illustrate the overall appearance and distinct characteristics of the new *Miscanthus* cultivar 'MBS 1001'.

FIG. 3 shows 'MBS 1001' and 'MBS 1002' flower timing comparisons. The photograph in FIG. 3 was taken in early fall, $1^{st}$ year growth at Davis, Calif., and indicates early panicle/flower coloration of 'MBS 1001' compared to 'MBS 1002'. The photograph in FIG. 4 was taken in mid fall, $1^{st}$ year growth, Davis, Calif., which also shows that 'MBS 1001' flowers earlier than 'MBS 1002'. The photograph in FIG. 5 shows that the flowers of 'MBS 1002' caught up to those of 'MBS 1001' in late fall, $1^{st}$ year growth, Davis, Calif..

DETAILED BOTANICAL DESCRIPTION OF THE PLANT

Figure 1:
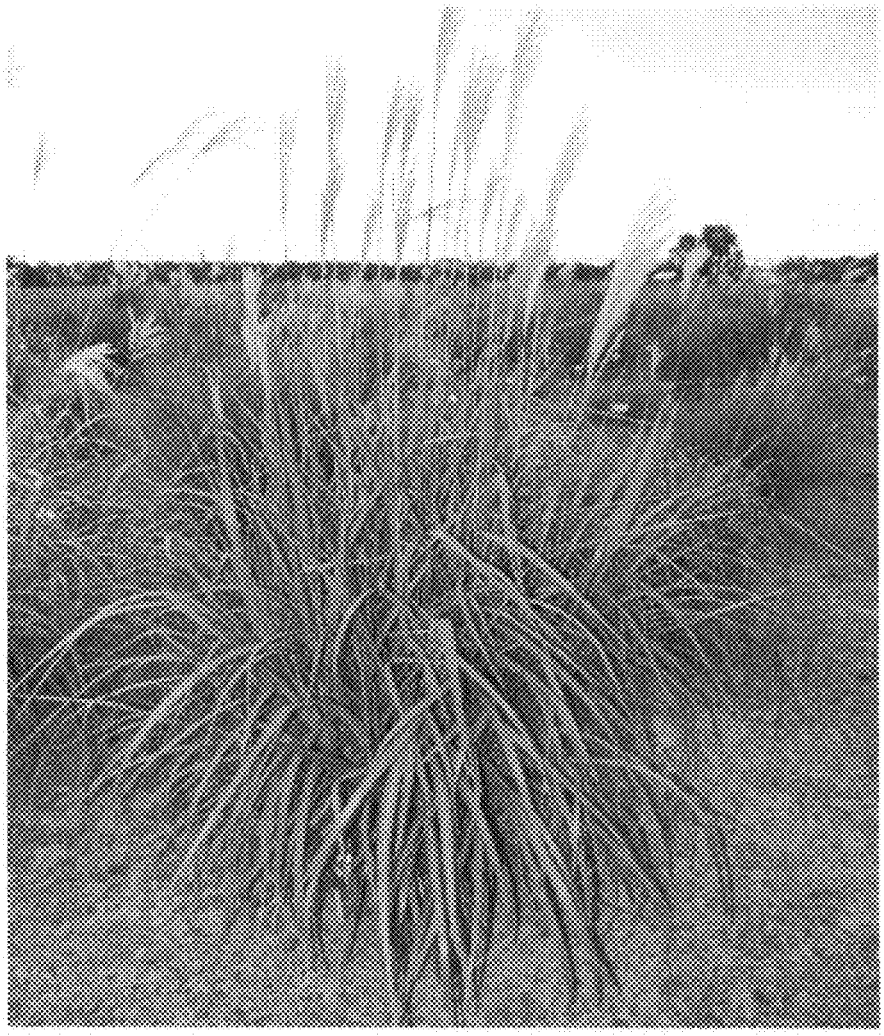
FIG. 1 depicts 'MBS 1001' ('MDL 1001') in mid-summer of $2^{nd}$ year growth at Tifton, Ga. Plants were under dryland growing conditions and experienced extreme drought and heat stress in early summer. Plant height at base of tallest flowering culm is ~2.2 m.
Figure 2:
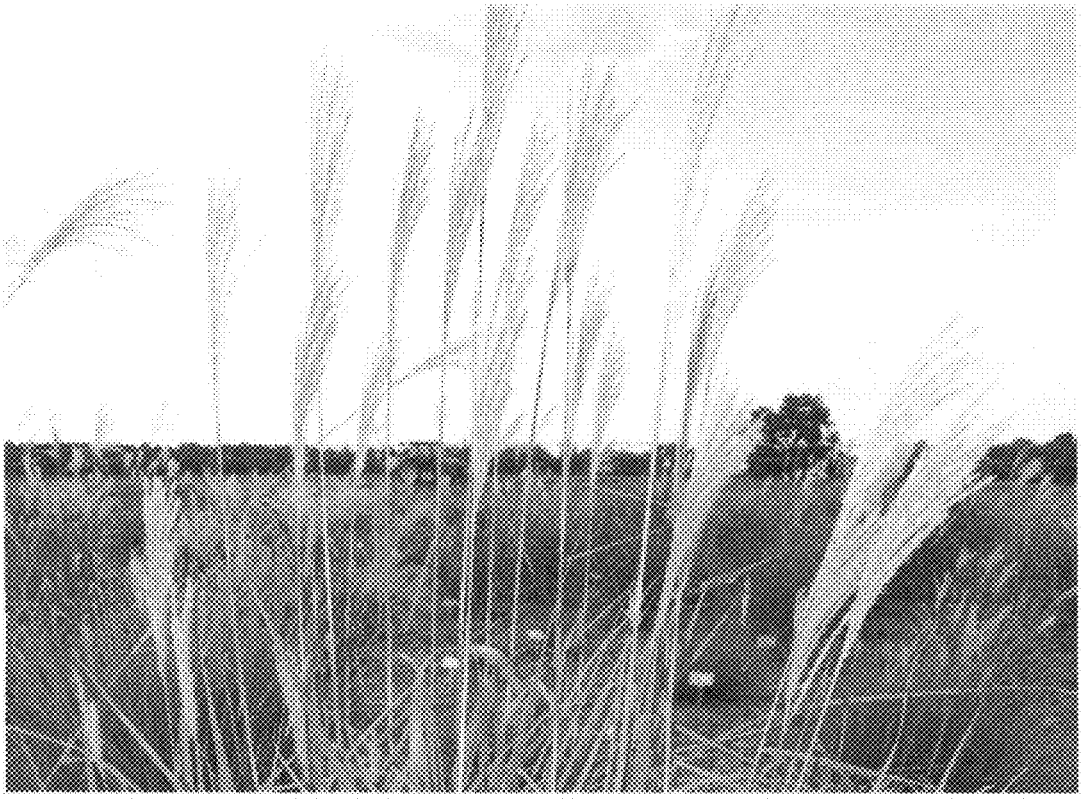
FIG. 2 depicts 'MBS 1001' in mid-summer of $2^{nd}$ year growth at Tifton, Ga. The figure illustrates mature unfertilized panicles of 'MBS 1001'. The 'MBS 1001' plants in the photograph were harvested by removing above-ground biomass approximately 12 cm above ground level in the previous year, and thus the biomass visible in this photograph represents annual, rather than cumulative, growth.
Figure 3:
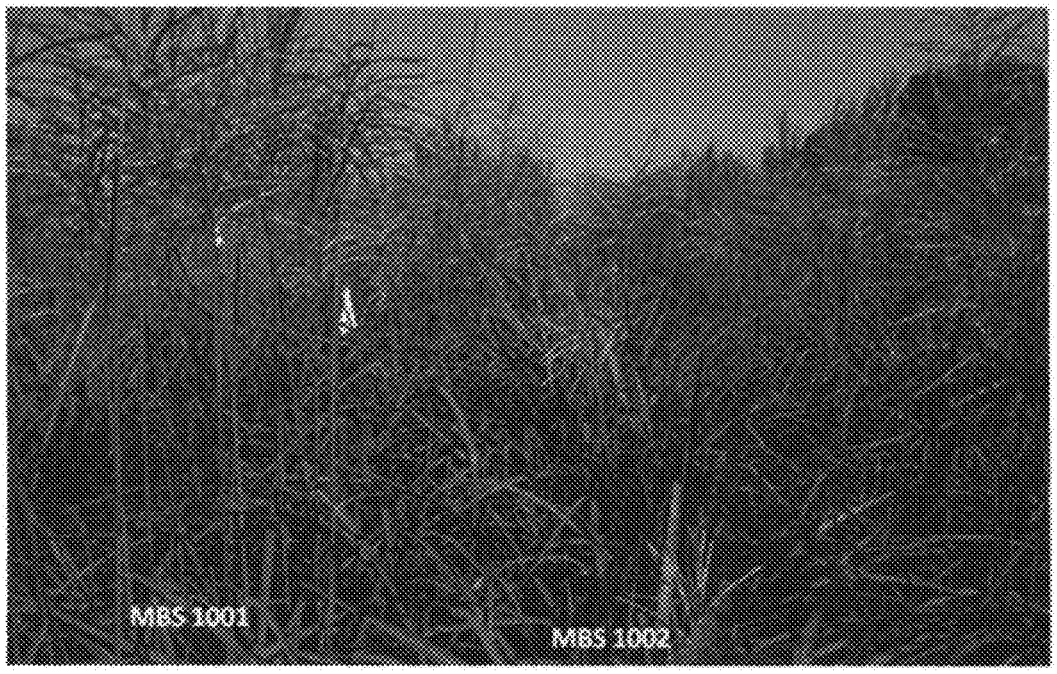
FIGS. 3 to 5 indicate fall flower comparisons of the sister lines 'MBS 1001' and 'MBS 1002' at Davis, Calif. after first year growth under irrigation management.
Figure 4:
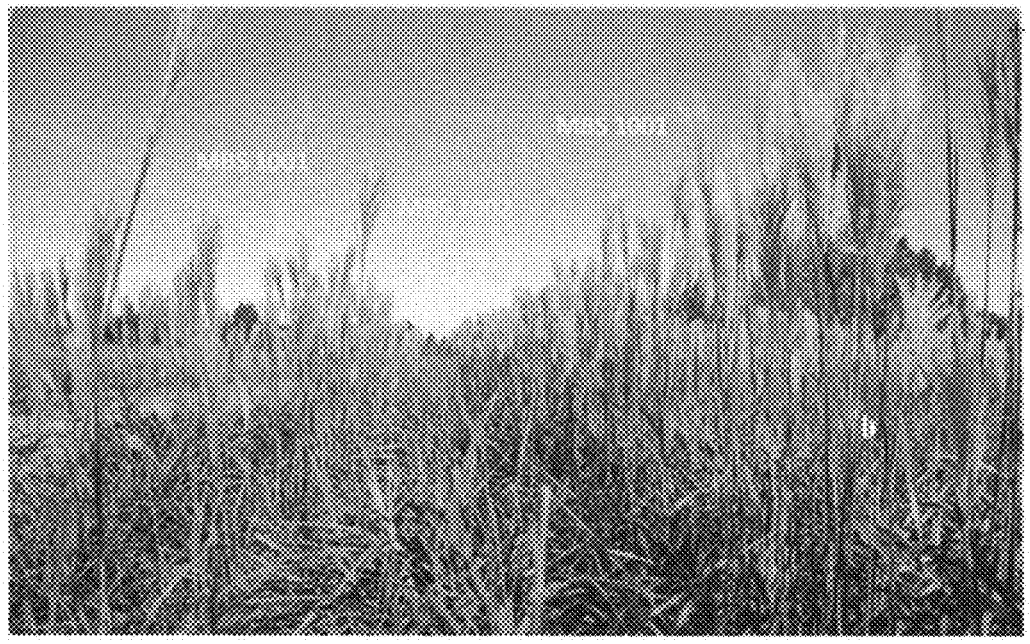
Figure 5:
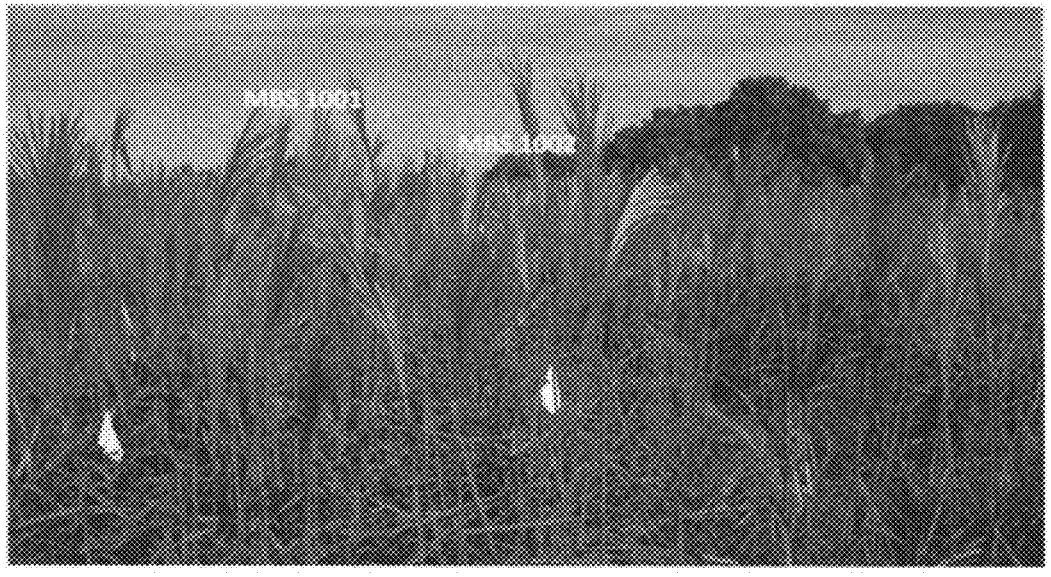

'MBS 1001' has not been observed under all possible environmental conditions, and the phenotype may vary significantly with variations in environment. The following observations, measurements, and comparison describe this plant as grown at Klein-Wanzleben, Germany, when grown in the field, unless otherwise noted. All observations were recorded during the plant's dormant season (April 2008) and during the 2007 and 2008 growing season unless otherwise noted. The color determination is in accordance with The 1995 R.H.S. Colour Chart of The Royal Horticultural Society, London, England, except where general color terms of ordinary dictionary significance are used. Plants for the botanical measurements in the present application are two and three-year old plants. These plants would be considered mature plants.

Botanical classification: 'MBS 1001' is a fertile hybrid of a cross from *Miscanthus sinensis* and *Miscanthus sacchariflorus*.

Common name: Maiden grass.

Parentage: Polycross of single *M. sacchariflorus* (the female parent) and several *M. sinensis* male pollen plants.

General description:

*Blooming period*.—'MBS 1001' blooms in mid to late fall in the Southern and Central US. Blooms/mature panicles are retained over the winter and seed shattering can occur. Flowering is delayed later into the fall at northern most latitudes of Europe and Canada. Blooming period may initiate earlier in the season depending on drought and heat stress conditions. The severity of stress can dictate earliness in panicle proliferation. Generally, early to mid-summer flowering ceases for a period and new flowering culms will continue to develop into the fall.

*Plant habit*.—Herbaceous, tuft forming, biomass grass with upright culms. 17-20 leaves per culm.

*Height and spread*.—Top leaf height ~3.0-3.2 meters.

*Hardiness*.—Productive growth in Klein-Wanzleben (north central), Germany; Ontario, Canada; Davis, Calif.; Tifton, Ga; Lafayette, Ind.; Champaign, Ill.; Franklin, Ky..

*Culture*.—Best in sandy loam, well-drained soil, higher yields at higher soil fertility.

*Diseases and pests*.—In the United States, 'MBS 1001' has shown excellent resistance to lesser stem borer spp. when compared to the public check variety *M.×giganteus* cv. 'Illinois'. Observations and confirmation on stem borer tolerance occurred during early stages within 2-8 weeks after planting of seedling material. This has been observed across at least 7 locations, particularly in the Southeastern US.

*Root description*.—Fibrous, well branched and dense with fast-developing creeping rhizomes, with shoots arising about 5-15 cm from base of the culms.

Growth and propagation:

*Propagation*.—In vitro: By culm division, culture from rhizomes, meristem or axillary buds (nodes). In vivo: By culm division containing meristem or axillary buds, rhizomes, and by seed.

*Growth rate*.—Parent comparison: More vigorous than *sacchariflorus* parent, and more vigorous than the *sinensis* poly male average.

Culm (stem) description: (Plant ages for data below are from two and three year old plants. They would be considered mature plants.)

*General*.—Cylindrical, pithy, reed-like, erect, sheathed.

*Culm aspect*.—Rigid and held erect, none are cascading.

*Culm color* (*dormant season*).—Yellowish, lower internodes partly reddish. Midsummer color is yellow green (RHS 144C or 144D), lower internodes partly reddish orange (RHS 165B or 165C or 165D, and varies with intensity depending on location latitude, growing conditions, and time of observation. Culm size: average about 0.9 cm in diameter.

*Culm circumference*.—2.4 cm.

*Culm height*.—2.8 m.

*Basal circumference* 2 *yr*.—95 cm.

*Culm surface*.—Culm is pubescent on the green leaf sheaths.

*Internode length*.—8 to 22 cm.

*Ligule*.—Membranous, ~3 mm (*M.×giganteus* cv. 'Illinois' is 2.5-3 mm); color reddish, RHS 145 A; border RHS 59B; longest hair is 2 mm (*M.×giganteus* cv. 'Illinois' is 1 mm), encircles the entire culm; inner surface is glabrous but pubescent on the outer surface; long pubescence are mainly on the side, and hairs on the side are approximately 8 mm (*M.×giganteus* cv. 'Illinois' hairs are about 4-5 mm).

Foliage description:

*Leaf shape*.—Linear.

*Leaf base*.—Sheathed.

*Leaf division*.—Simple.

*Leaf apex*.—Acuminate.

*Leaf aspect*.—Emerging leaves are erect, blades are convex, leaf angle younger leaves 50°, leaf angle older leaves 5°, color code RHS 141A or 141B on both upper and lower leaf surfaces.

*Leaf tip younger leaves*.—½ pendent, meaning approximately half of the leaf tip area if the younger leaves bends downward.

*Leaf venation*.—Parallel, upper surface concave, lower surface convex.

*Leaf margins*.—Entire, visible, sharp short bristles under the microscope.

*Leaf size*.—Up to 100 cm, width: 2-3.2 cm.

*Leaf attachment*.—Sheathed.

*Leaf arrangement*.—Alternate, tapering.

*Leaf surface*.—Upper-light glossy, lower-matte, single hairs on some leaves on the lower surface.

*Leaf color* (*during growing season*).—Green, no stripes. Leaf color changes slightly over time of growing season or age of leaf. In early to mid season expect to observe a leaf color of RHS 141A or 141B on both upper and lower surfaces. Pre-senescence late summer to expresses a leaf color of RHS 141C and D on both upper and lower leaf. Fall winter senescence color expression to be RHS 164B or 164C. No hairs on lower leaf surface.

Flower and reproductive organ description:

*General description*.—Compact, fan-shaped panicle terminating from each culm in mid to late September, composed of numerous slender, silky aggregate racemes.

*Persistence of inflorescence*.—Panicles are persistent from fall through winter.

*Fragrance*.—None.

*Panicle size*.—Average of 25 cm in length and 34 cm in width.

*Angle of raceme*.—30°-40°.

*Panicle color*.—Varies from RHS 152D-175B when panicle is developing (1 month) to RHS 2D when mature. The intensity of these color grades depends on location and growing conditions. However, this color report indicates that RHS 175B would be early panicle appearance and RHS 152D is for more mature panicle appearance and RHS 2D is post-shatter appearance.

*Spikelet description*.—Spikelet in pairs.

*Spikelet size*.—About 5 mm in length and 1 mm in width (excluding hairs).

*Spikelet color*.—RHS 153B.

*Spikelet hairs*.—12 mm in length, RHS 158C in color.

*Awn size*.—1-2 mm.

Reproductive organ description:

*Androecium*.—Anthers; 3-5 mm in length and 0.5 mm in width, red in color, RHS 187C.

*Gynoecium*.—Stigma color is RHS 187A, red, 4 mm in length and 0.5 mm in width.

*Caryopsis*.—Produces fertile seeds. 'MBS 1001' has a small elliptical seed, which is a heavy anemochore with an average seed weight of 0.96 mg, a chamaephyte (buds permanently above ground) life form, with an annual seed production of 64-1200 seeds per plant depending upon pollen source availability. Healthy seeds are clear amber to dark brown RHS 167B-200A.

Biomass yield performance: Table 1 summarizes dry tons per acre, average basal circumference, average compression circumference, average culm diameter, average culm length of 'MBS 1001', and flower maturity ratings compared to *M.×giganteus*, cv. 'Illinois', and three patent applied sister lines over several locations. Data represents 2-year mature *Miscanthus* yield performances across six locations throughout the target growing regions for perennial biomass production.

Although 'MBS 1001' was only statistically higher yielding than its sister line 'MBS 7003', it was consistent in yield performance, and did as well or better than the commercial sterile check cultivar, 'Illinois'. Basal circumference was significantly less than 'Illinois' but greater than all three sister line comparisons. 'MBS 1001' was significantly greater than 'Illinois' for both compressed circumference and culm diameter, and similar to its sister line comparisons for these two yield type traits. The later flowering cultivar was 'Illinois' when compared to the MBS lines. However, flower maturity is where additional variation among the sister lines also occurs. Of the four fertile MBS lines, 'MBS 7003' flowers and matures its panicles the earliest, followed by 'MBS 1001' which indicates a more medium maturity when compared to 'MBS 7002', and 'MBS 1002'.

TABLE 1

Two-year, six US location yield and plant data for MBS cultivar performances for 'MBS 7002', 'MBS 7003', 'MBS 1001', and 'MBS 1002'.

| Material Name | Yield (dton/ac) | Rk | % Moisture | Basal Circum-ference (Bcirc) cm | Compressed Circum-ference (CCirc) cm |
|---|---|---|---|---|---|
| 'MBS 1001' | 8.01 | 1 | 24.8 | 90.6 | 31.1 |
| 'MBS 7002' ('Lake Erie') | 7.90 | 2 | 24.8 | 86.3 | 29.1 |
| 'Illinois' | 7.71 | 3 | 23.2 | 114.4 | 25.9 |
| 'MBS 1002' | 7.34 | 4 | 25.6 | 88.5 | 33.4 |
| 'MBS 7003' ('Columbia') | 7.15 | 5 | 26.6 | 87.9 | 32.5 |
| Grand Mean | 5.67 | | 23.8 | 92.7 | 26.4 |
| Locs × Years | (6 × 2) 12* | | (6 × 2) 12 | (5 × 1) 5** | (6 × 1) 6*** |
| LSD(.05) | 0.81 | | 2.7 | 5.3 | 3.4 |
| CVErr | 13.3 | | 16.4 | 5.2 | 13.1 |
| CVExL | 28.4 | | 23.0 | 7.1 | 17.7 |

TABLE 1-continued

Two-year, six US location yield and plant data for MBS cultivar performances for 'MBS 7002', 'MBS 7003', 'MBS 1001', and 'MBS 1002'.

| Material Name | Culm Diameter (CmD) mm | Culm Length (CmL) cm | Flower Maturity Rating |
|---|---|---|---|
| 'MBS 1001' | 8.6 | 248.5 | 3.0 |
| 'MBS 7002' ('Lake Erie') | 7.6 | 247.0 | 4.0 |
| 'Illinois' | 7.3 | 260.8 | 5.0 |
| 'MBS 1002' | 9.0 | 239.7 | 4.0 |
| 'MBS 7003' ('Columbia') | 8.4 | 213.5 | 2.0 |
| Grand Mean | 7.5 | 218.5 | 3.6 |
| Locs × Years | (6 × 1) 6 | (5 × 1) 5 | (6 × 1) 6 |
| LSD(.05) | 1.0 | 9.4 | 0.2 |
| CVErr | 13.8 | 3.9 | 7.8 |
| CVExL | 18.3 | 5.3 | 8.5 |

Grand Mean: Trial mean (Combined years and US locations)

Locs × Years: Number of years and US locations for derivation of statistical values.

CVErr: coefficient of variation for entire error term of analysis.

CVExL: coefficient of variation error-location effects.

*Refers to that the mean value was calculated based on data collected from 6 locations in two years, therefore 12 total observations were made.

**Refers to that the mean value was calculated based on data collected from 5 locations in one year, therefore 5 total observations were made.

***Refers to that the mean value was calculated based on data collected from 6 locations in one year, therefore 6 total observations were made.

It is claimed:

1. A new and distinct cultivar of *Miscanthus* plant named 'MBS 1001' substantially as herein shown and described.

* * * * *